United States Patent
Lim et al.

(10) Patent No.: US 8,149,409 B2
(45) Date of Patent: Apr. 3, 2012

(54) APPARATUS AND METHOD FOR ON-LINE DETECTING WELDING PART OF STRIP

(75) Inventors: Choong-Soo Lim, Kyungsangbook-do (KR); Ki-Sam Son, Kyungsangbook-do (KR); Kwang-Ho Son, Kyungsangbook-do (KR); Sang-Jin Lee, Kyungsangbook-do (KR); Seung-Gap Choi, Kyungsangbook-do (KR); Ki-Jang Oh, Kyungsangbook-do (KR)

(73) Assignee: Posco (KR)

( * ) Notice: Subject to any disclaimer, the term of this patent is extended or adjusted under 35 U.S.C. 154(b) by 757 days.

(21) Appl. No.: 12/097,646

(22) PCT Filed: May 26, 2006

(86) PCT No.: PCT/KR2006/002001
§ 371 (c)(1),
(2), (4) Date: Sep. 16, 2008

(87) PCT Pub. No.: WO2007/073023
PCT Pub. Date: Jun. 28, 2007

(65) Prior Publication Data
US 2009/0279096 A1    Nov. 12, 2009

(30) Foreign Application Priority Data
Dec. 23, 2005  (KR) .................. 10-2005-0129072

(51) Int. Cl.
| G01N 21/55 | (2006.01) |
| G01N 21/86 | (2006.01) |
| G01B 11/24 | (2006.01) |
| G01B 11/14 | (2006.01) |
| G01V 8/00  | (2006.01) |

(52) U.S. Cl. ... 356/445; 356/601; 356/614; 250/559.01; 250/559.4

(58) Field of Classification Search ....................... None
See application file for complete search history.

(56) References Cited

U.S. PATENT DOCUMENTS

| 4,121,087 | A | * | 10/1978 | Malmuth et al. ......... 219/121.62 |
| 4,578,561 | A | * | 3/1986 | Corby et al. ............. 219/124.34 |
| 4,734,766 | A | * | 3/1988 | Shiozumi et al. ............. 382/141 |
| 5,150,175 | A | * | 9/1992 | Whitman et al. ............. 356/429 |
| 5,245,409 | A | * | 9/1993 | Tobar ............................ 356/606 |
| 5,442,155 | A |   | 8/1995 | Nihei et al. |
| 5,570,187 | A |   | 10/1996 | Nihei et al. |

(Continued)

FOREIGN PATENT DOCUMENTS
DE    20214969 U1 *  3/2004
(Continued)

*Primary Examiner* — Tarifur Chowdhury
*Assistant Examiner* — Gordon Stock, Jr.
(74) *Attorney, Agent, or Firm* — The Webb Law Firm

(57) ABSTRACT

There is provided an on-line detection system and method for a weld of a steel strip, which can emit a laser beam onto the surface of a steel strip moving at a high speed and measure the reflectivity of the laser beam reflecting from the same, thereby detecting the weld of the steel strip easily on-line. In the on-line detection system, reflectivity measuring means emits a laser beam onto a moving steel strip and continuously measuring the reflectivity of the laser beam returning from the surface of the steel strip, and signal processing means detects a weld of the steel strip based on change in the reflectivity measured on the weld.

11 Claims, 6 Drawing Sheets

U.S. PATENT DOCUMENTS

| | | | |
|---|---|---|---|
| 5,714,762 A * | 2/1998 | Li et al. ................ 250/559.2 |
| 5,978,090 A * | 11/1999 | Burri et al. ................ 356/613 |
| 6,399,915 B1 * | 6/2002 | Mori et al. ............ 219/121.83 |
| 6,563,575 B1 * | 5/2003 | Nichols et al. ............ 356/237.1 |
| 6,909,799 B1 * | 6/2005 | Wildmann et al. ........... 382/152 |
| 6,937,329 B2 * | 8/2005 | Esmiller ................ 356/237.2 |
| 7,129,438 B2 * | 10/2006 | Bates et al. ............ 219/121.63 |
| 7,236,255 B2 | 6/2007 | Kodama et al. |
| 7,577,285 B2 * | 8/2009 | Schwarz et al. ............ 382/141 |
| 2002/0015148 A1 * | 2/2002 | Tomomatsu ............ 356/237.2 |
| 2004/0011773 A1 * | 1/2004 | Fritz et al. ............ 219/121.83 |

FOREIGN PATENT DOCUMENTS

| | | | |
|---|---|---|---|
| EP | 100721 A * | 2/1984 |
| JP | 55106510 A | 8/1980 |
| JP | 56119670 A | 9/1981 |
| JP | 59028608 A | 2/1984 |
| JP | 60056205 A * | 4/1985 |
| JP | 6425748 U | 2/1989 |
| JP | 7116849 A | 5/1995 |
| JP | 8193811 A | 7/1996 |
| JP | 10096604 A * | 4/1998 |
| JP | 2003322513 A | 11/2003 |

* cited by examiner

[Fig. 1]
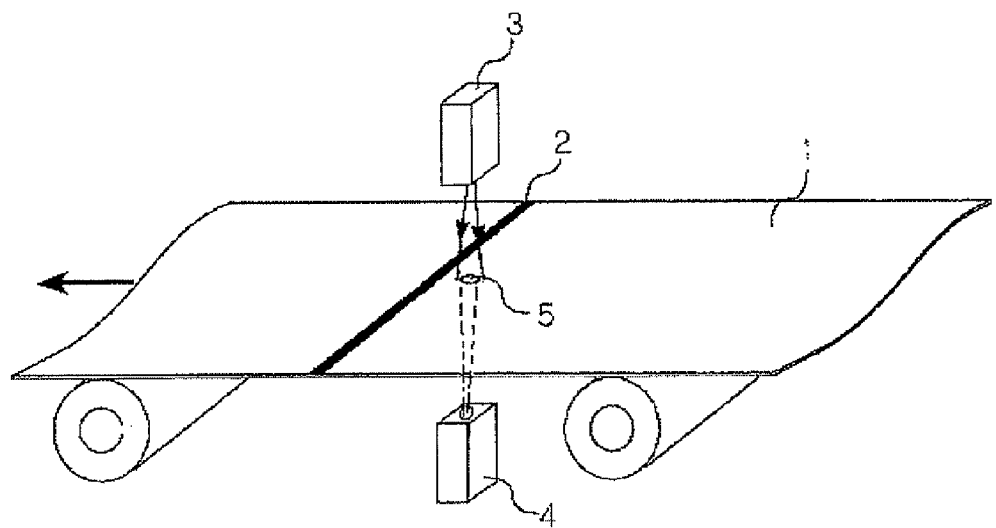
Prior Art
[Fig. 2]
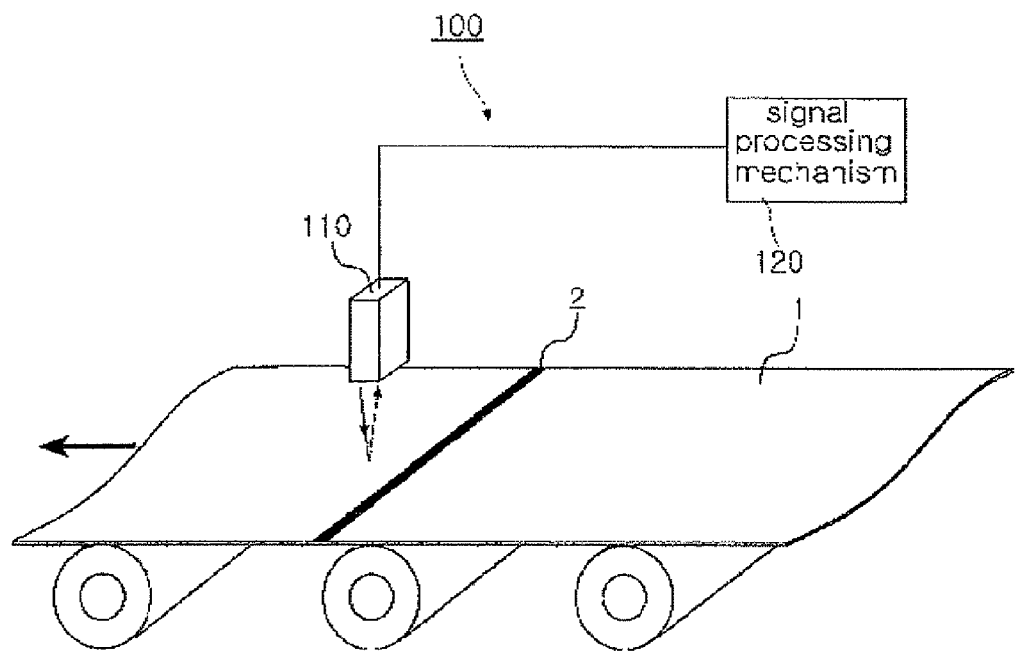

[Fig. 3]
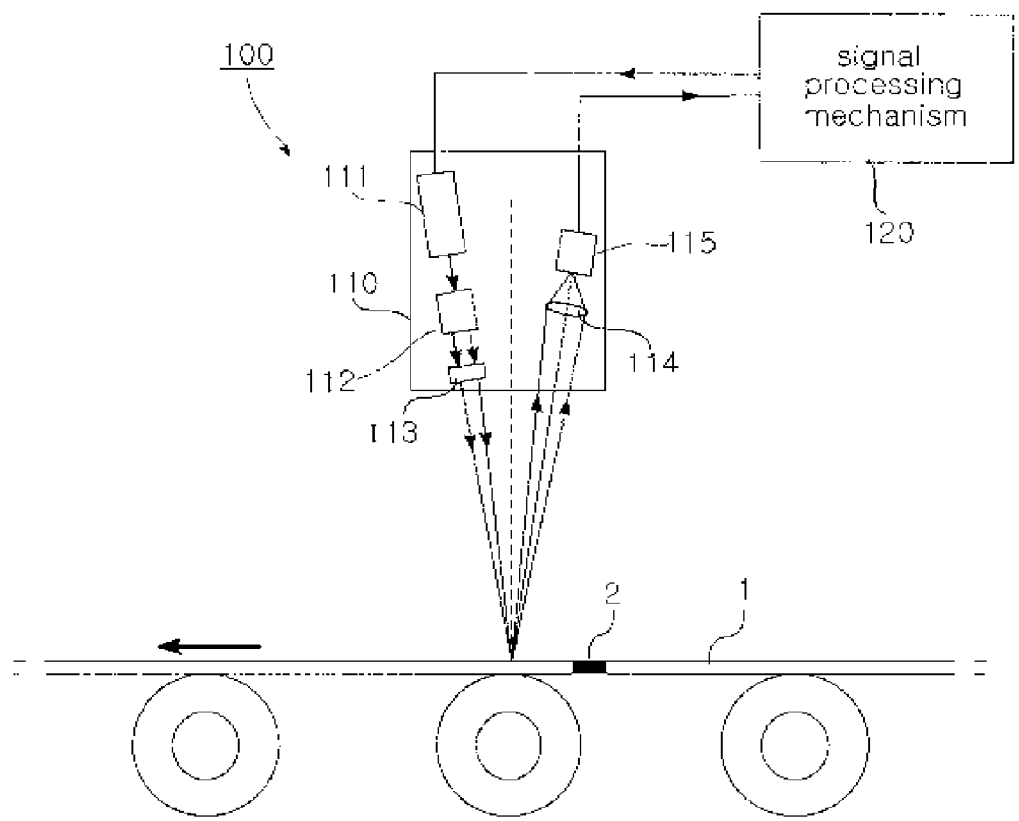
[Fig. 4]
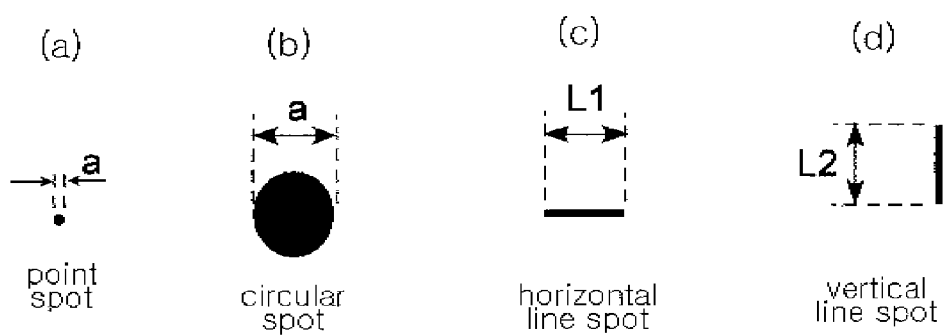

[Fig. 5]
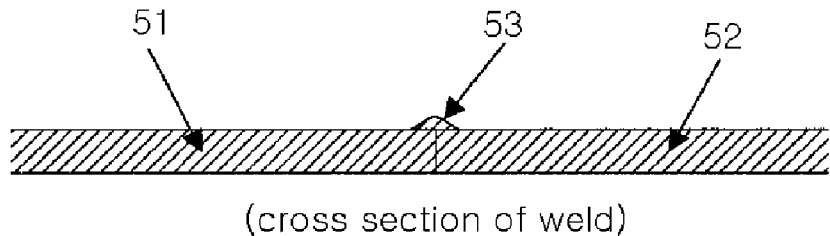
(cross section of weld)
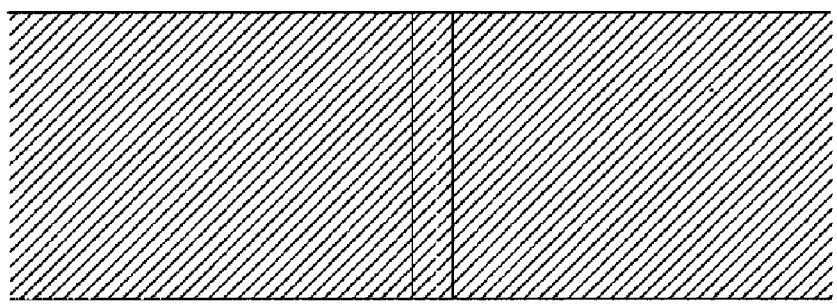
(top surface of welded steel strip)
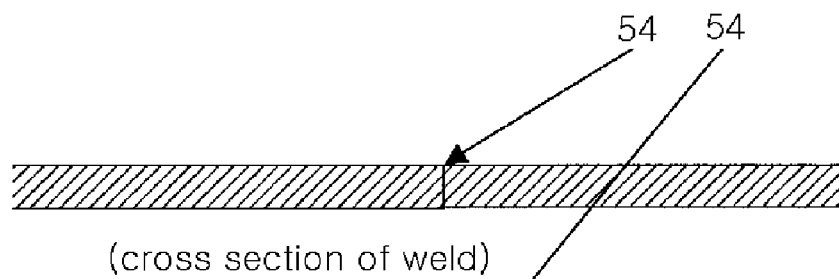
(cross section of weld)
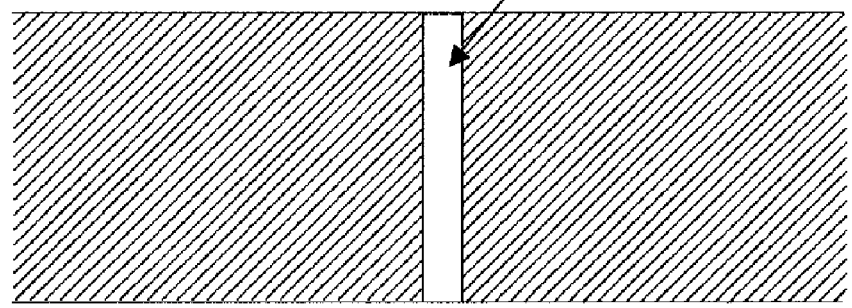
(top surface of welded steel strip)

[Fig. 6]
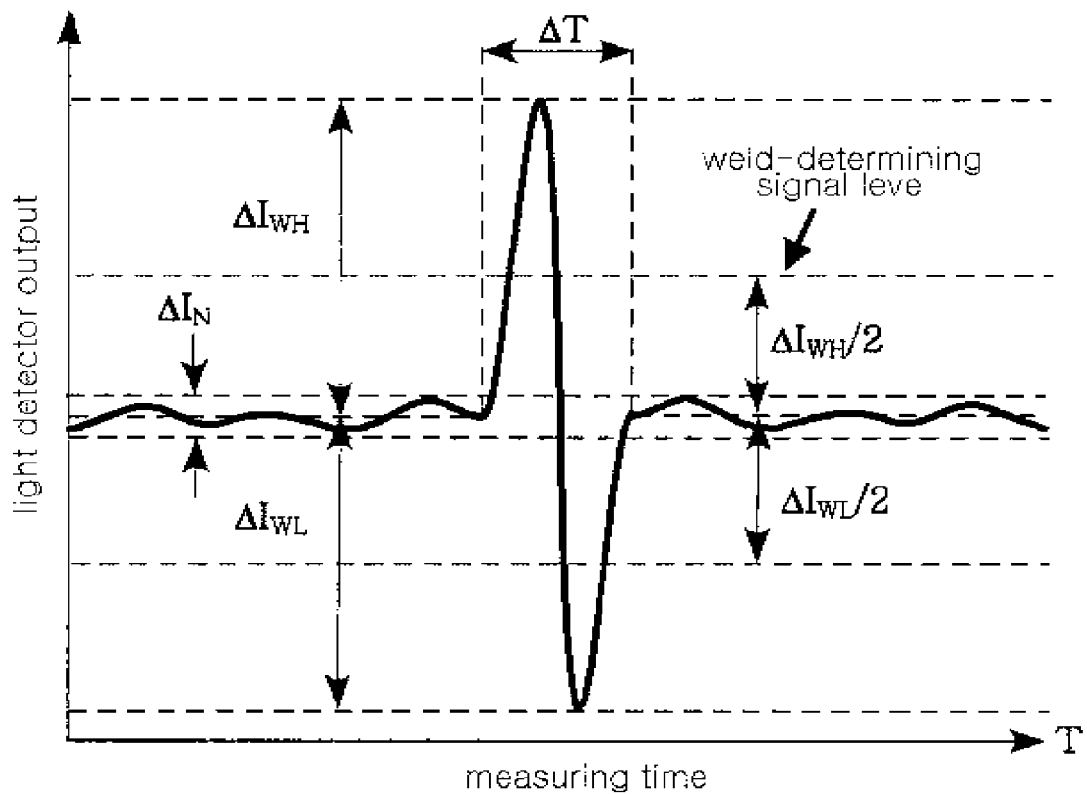
[Fig. 7]
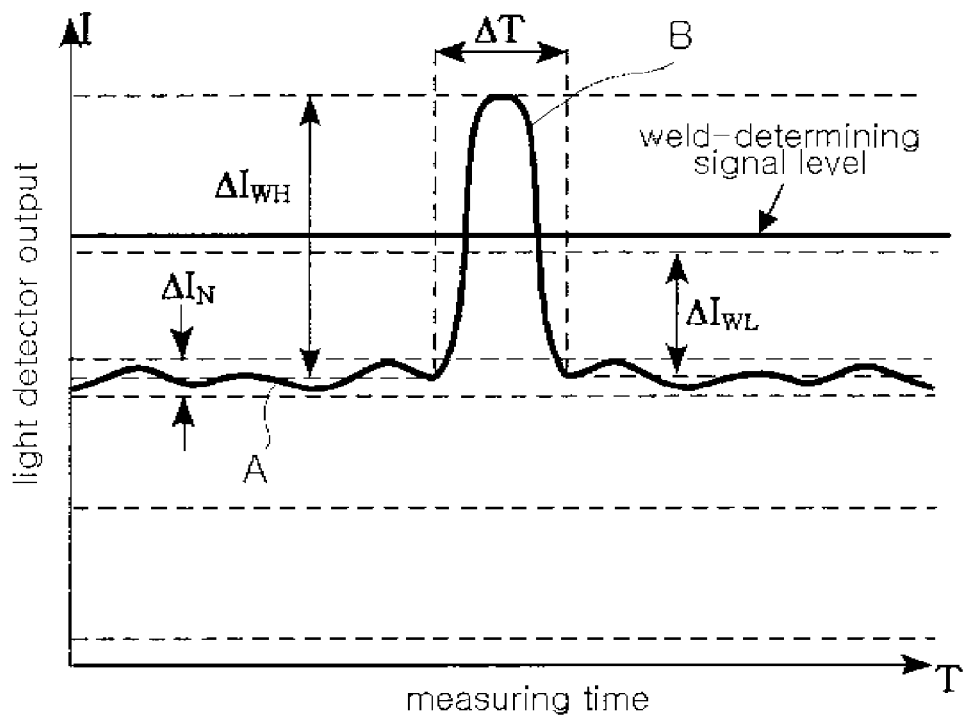

[Fig. 8]
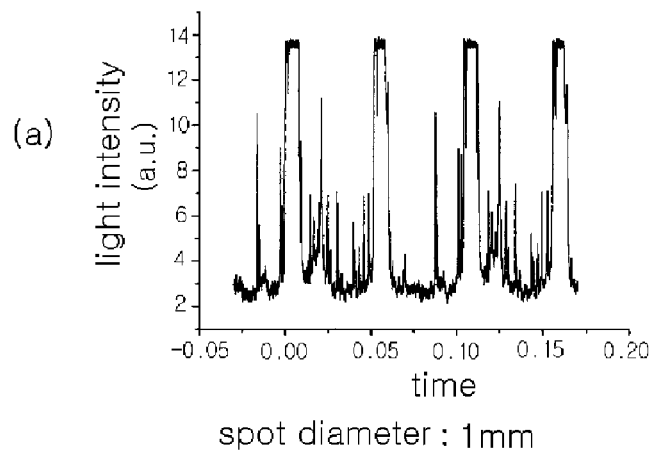
(a) spot diameter : 1mm
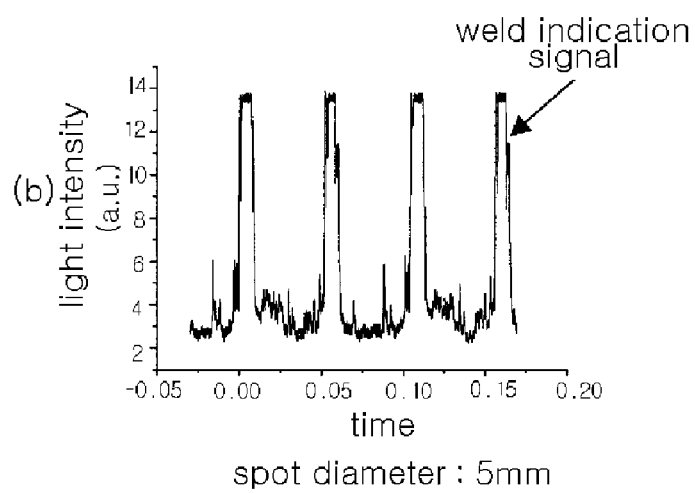
(b) spot diameter : 5mm
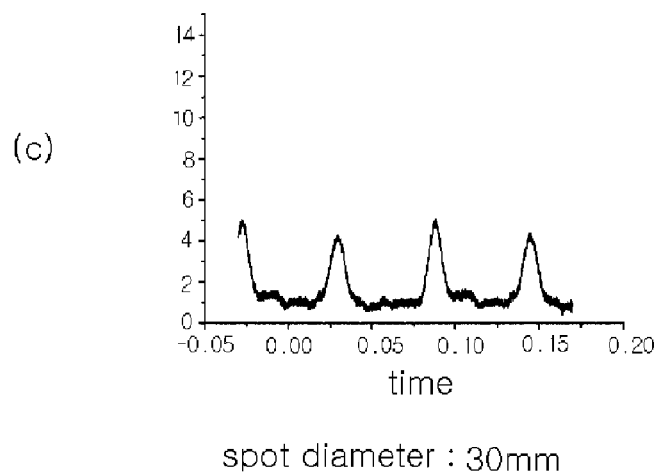
(c) spot diameter : 30mm

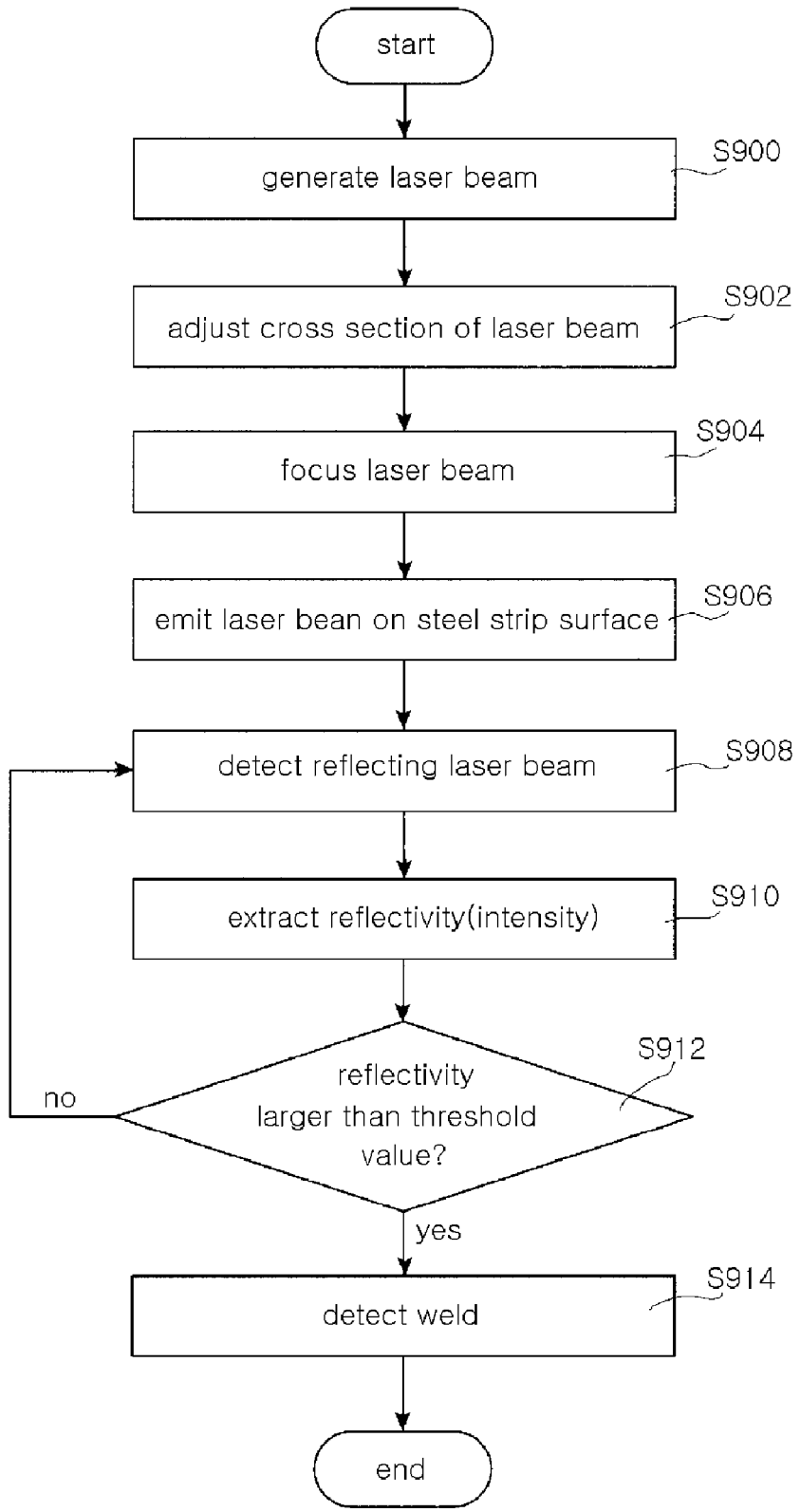

APPARATUS AND METHOD FOR ON-LINE DETECTING WELDING PART OF STRIP

TECHNICAL FIELD

The present invention relates to an on-line detection system and method for a weld of a steel strip, in particular, which scans a laser beam onto a steel strip moving at a high speed, and based on the reflectivity of the laser beam returning from the steel strip, locates on-line a weld of the steel strip.

BACKGROUND ART

Generally, in a cold rolling of an iron and steel mill, unit coils are welded together into a steel strip at a starting step of the cold rolling so that continuous rolling can be carried out, and the steel strip is cut along welds into the unit coils at a finishing step of the cold rolling, which are then transported to a following process or shipped as final products. Accordingly, in the cold rolling, it is inevitably required to locate such welds in order to automatically and precisely control essential process equipments and trim the steel strip along the welds into the unit coils at the output side.

FIG. 1 is a detection system for a weld of a steel strip using a through hole according to the prior art.

Referring to FIG. 1, the conventional detection system for a weld of a steel strip has a light projector 3 and a light detector 4 arranged above and under a moving steel strip 1 that is being transported. The light projector 3 is arranged in a position where detection on a weld 2 is needed, and illuminates light downward onto the steel strip 1. The light detector 4 arranged under the steel strip 1 detects the light passing through a hole 5 perforated in the steel strip 1, thereby detecting a corresponding weld 2.

Such a conventional detection system needs the hole 5 perforated adjacent to the weld 2 in order to detect the weld 2. However, this also needs to temporarily stop a corresponding line to perforate the steel strip 1, and thus productivity is lowered. In addition, excess metal formed around the hole 5 damages or scratches the surface of a feed roll or mill roll. Then, the scratched roll disadvantageously transfers a mark onto the surface of a following steel strip. Where the steel strip 1 is very thin or high carbon steel, the hole 5 may fracture the steel strip 1.

Furthermore, in the conventional weld detection system using a hole, the light projector 3 installed above the steel strip 1, which is being transported for process, uses a general light source. Such a light source has a short lifetime and thus needs periodic replacement. Since the light detector 4 is installed below the steel strip 1 to detect light passing through the hole 5, the detection system is difficult to install but easily soiled by dropping dust or foreign materials.

The present invention has been made to solve the foregoing problems of the prior art which detects a weld using a through hole. Therefore, an object of certain embodiments of the present invention is to provide an on-line detection system and method for a weld of a steel strip, which can emit a laser beam onto the surface of a steel strip moving at a high speed and measure the reflectivity of the laser beam reflecting from the same, thereby detecting the weld of the steel strip easily on-line without having to form the through hole.

SUMMARY OF THE INVENTION

According to an aspect of the invention for realizing any of the objects, there is provided an on-line detection system for a weld of a steel strip. The on-line detection system includes: reflectivity measuring means for emitting a laser beam onto a moving steel strip and continuously measuring the reflectivity of the laser beam returning from the surface of the steel strip; and signal processing means for detecting a weld of the steel strip based on change in the reflectivity measured on the weld.

According to an embodiment of the invention, it is preferable that the reflectivity measuring means emits the laser beam continuously at an angle ranging from 80° to 100° with respect to the surface of the steel strip. More preferably, the reflectivity measuring means emits the laser beam perpendicularly to the surface of the steel strip.

According to an embodiment of the invention, the reflectivity measuring means includes a laser beam generator for generating the laser beam; a focusing lens for focusing the laser beam; a collecting lens for collecting the laser beam reflecting from the surface of the steel strip; and a light detector for outputting an electric signal corresponding to the reflectivity of the collected laser beam. Here, the reflectivity measuring means may further include a beam adjuster for adjusting the cross section of the laser beam generated by the laser beam generator, in which the beam-adjusting means are arranged between the laser beam generator and the focusing lens.

According to an embodiment of the invention, the beam adjuster preferably adjusts the laser beam emitted onto the surface of the steel strip into a circular spot having a diameter of 4 mm to 6 mm or a line spot having a width of 2 mm to 5 mm and a length of 30 mm to 50 mm.

According to an embodiment of the invention, the focusing lens may include a spherical lens or a cylindrical lens.

According to an embodiment of the invention, the laser beam emitted onto the surface of the steel strip may have a shape selected from the group consisting of point, circle and line.

According to an embodiment of the invention, the signal processing means determines a specific point on the surface of the steel strip as the weld if the reflectivity of the laser beam returning from the specific point is out of a preset threshold value.

According to an aspect of the invention for realizing any of the objects, there is provided an on-line detection method for a weld of a steel strip, including steps of: (a) emitting a laser beam onto the surface of a steel strip which is being transported; (b) continuously detecting the laser beam reflecting from the surface; (c) measuring the reflectivity of the reflecting laser beam; and (d) locating the weld based on change in the reflectivity.

According to an embodiment of the invention, the step (a) generates the laser beam and focuses the laser beam to emit onto the steel strip being transported. Here, the step (a) may further comprise adjusting the cross section size of the laser beam generated.

According to an embodiment of the invention, the step (a) emits the laser beam perpendicularly onto the surface of the steel strip.

According to an embodiment of the invention, the step (d) determines a specific point on the surface of the steel strip as the weld if the reflectivity of the laser beam returning from the specific point is out of a preset threshold value.

According to certain embodiments of the invention as set forth above, a weld moving at a high speed can be easily detected on-line without using a through hole as in the prior art.

Furthermore, according to certain embodiments of the invention, since a through hole is not necessary, productivity of cold rolled products can be enhanced and problems such as marking and fracture can be essentially excluded.

Moreover, according to certain embodiments of the invention, it is possible to detect a weld easily and precisely on-line by emitting a laser beam continuously onto a steel strip and locating the weld based on the reflectivity difference between the weld and an ordinary steel strip surface.

BRIEF DESCRIPTION OF THE DRAWINGS

FIG. 1 is a configuration view illustrating a detection system for a weld of a steel strip using a through hole according to the prior art;

FIG. 2 is a schematic configuration view illustrating an on-line detection system for a weld of a steel strip according to an embodiment of the invention;

FIG. 3 is a detailed configuration view of the on-line detection system for a weld of a steel strip of the invention;

FIGS. 4 (a)-(d) are top views illustrating examples of laser beam spots focused onto the surface of a steel strip according to an embodiment of the invention;

FIG. 5 is a sectional view illustrating a weld shape formed by a flash butt welding according an embodiment of the invention;

FIG. 6 is a graph illustrating a weld detection signal by a laser reflection measuring mechanism according to an embodiment of the invention;

FIGS. 7 and 8 are graphs illustrating examples of laser reflection signals detected on a weld by the on-line detection system according to an embodiment of the invention; and FIG. 9 is a flowchart illustrating an on-line detection method for a weld of a steel strip according to an embodiment of the invention.

BEST MODE FOR CARRYING OUT THE INVENTION

Hereinafter preferred embodiments of the invention will be described in detail with reference to the accompanying drawings.

FIG. 2 is a schematic configuration view illustrating an on-line detection system for a weld of a steel strip according to an embodiment of the invention.

Referring to FIG. 2, the on-line detection system 100 for a weld of a steel strip of this invention includes a laser reflectivity measuring mechanism 110 and a signal processing mechanism 120. While a single one of the laser reflectivity measuring mechanism 110 is shown in the drawing, this is merely an illustrative embodiment of the invention. In another embodiment of the invention, two or more of the laser reflectivity measuring mechanism may be provided according to the width of the steel strip 1.

The laser reflectivity measuring mechanism continuously emits a laser beam onto a moving steel strip, which is being transported, and continuously measures the reflectivity of the laser beam returning from the surface of the steel strip. The reflectivity of the laser beam is preferably an index indicating the intensity of the laser beam reflecting from the surface of the moving steel strip 1, and detected different according to the reflectivity or absorbance of a steel strip itself, properties of a steel strip, surface roughness, surface irregularity, surface shape and so on.

The signal processing mechanism 120 synthetically analyzes the reflectivity of the laser beam measured by the laser reflectivity measuring mechanism 110 to locate the weld 2. The reflectivity (or intensity) of the laser beam reflecting from the surface of the steel strip 1 has a certain value when reflected from the weld 2 that is different from that of the laser beam reflected from other portions of the steel strip 1. Therefore, the reflectivity from other portions of the steel strip 1 is compared with that from the weld 2 in order to determine whether or not the weld 2 has passed the position onto which the laser beam is emitted. In this fashion, the signal processing mechanism 120 can detect the weld 2 of the steel strip 1 correctly and precisely by using the change in the reflectivity of the reflecting laser beam measured on the weld 2 of the moving steel strip 1.

Here, it is preferable that the laser reflectivity measuring mechanism 110 continuously emits the laser beam onto the surface of the steel strip 1 at an incident angle of 80° to 100°.

More preferably, the laser beam is emitted perpendicularly onto the surface of the steel strip 1. As the incidence angle of the laser beam onto the steel strip is closer to the right angle, the angle of the reflecting laser beam is also closer to the right angle. Then, the reflecting laser beam can be collected more efficiently, and it is easier to measure the reflectivity. That is, the reflecting laser beam is collected more when the incidence angle is closer to the right angle and the reflection angle of the laser beam is smaller since the laser beam reflecting and scattering from the surface of the steel strip 1 is collected to measure the reflectivity of the laser beam. Therefore, the reliability for the reflectivity measurement is higher when the laser beam is emitted substantially in the right angle.

FIG. 3 is a detailed configuration view of the on-line detection system for a weld of a steel strip of the invention.

Referring to FIG. 3, the on-line detection system for a weld of a steel strip according to this embodiment of the invention is generally constructed of the laser reflectivity measuring mechanism 110 and the signal processing mechanism 120. The laser reflectivity measuring mechanism 110 includes a laser beam generator 111, a focusing lens 113, a collecting lens 114 and a light detector 115. Alternatively, as shown in the drawing, the reflectivity measuring mechanism 110 may further include an aperture 112 for adjusting the sectional area of a laser beam.

The laser beam generator 111 generates a laser beam to be emitted onto the surface of the moving steel strip 1. The laser beam generator 111 generates the laser beam by emitting it for example through a semiconductor laser. Optionally, the aperture 112 may adjust the cross section of the laser beam. The aperture 112 may be located between the laser beam generator 111 and the focusing lens 113 to continuously adjust the cross section of the laser beam generated by the laser beam generator 111.

The focusing lens 113 focuses the laser beam whose cross section is adjusted by the aperture 112 so that the laser beam is emitted onto the surface of the moving steel strip 1. The focusing lens 113 may be a spherical lens or a cylindrical lens. Here, the shape of the laser beam emitted onto the steel strip may be varied according to the type of the focusing lens 113.

The collecting lens 114 collects the laser beam reflecting from the surface of the steel strip 1. The collecting lens 114 sends the laser beam reflecting from the surface of the steel strip 1 to the light detector 115.

The light detector 115, upon receiving the reflecting laser beam collected by the collecting lens 114, converts the laser beam into an electric signal corresponding to the reflectivity of the laser beam. That is, the light detector 115 preferably outputs an electric signal corresponding to the intensity of the reflecting laser beam. The light detector 115 may be a single detector or an array of detectors.

The electric signal corresponding to the reflectivity is sent from the light detector 115 to the signal processing mechanism 120, which detects the weld 2 of the steel strip 1 based on the electric signal. For example, when the electric signal at a specific point of the steel strip 1 is out of a preset critical value or change in the electrical signal at a specific point is out of a preset reference value, the specific point is determined as the weld 2.

FIG. 4 is a top view illustrating examples of laser beam spots focused onto the surface of a steel strip according to an embodiment of the invention.

As illustrated in FIG. 4, laser beam spots emitted onto the surface of the moving steel strip 1 may be variously shaped. Such a laser beam shape can be determined by the type of the focusing lens 113. For example, when the focusing lens 113 is spherical, the laser beam emitted onto the steel strip 1 would form a point or circular spot as shown in (a) and (b) of FIG. 4. When the focusing lens 113 is cylindrical, the laser beam emitted onto the steel strip 1 would form a horizontal or vertical line spot as shown in (c) and (d) of FIG. 4. While not shown in the drawing, as an alternative embodiment, the laser beam may be adapted to form a rectangle spot or a cross spot with two lines intersecting each other.

The size of each spot focused onto the surface of the steel strip 1 may be changed according to the focal length f of the focusing lens 113. For example, when the focusing lens 113 is spherical, the spot diameter a increases with the focal length of the spherical lens increasing relatively more than the distance between the spherical lens and the steel strip. Furthermore, when the focal length of the spherical lens is fixed, the spot diameter a increases in proportion to the diameter of the laser beam passing through the aperture 112. According to this embodiment, the spot diameter a can be adjusted easily through the aperture 112 and the focal length of the spherical lens.

Likewise, when the focusing lens 113 is cylindrical, a line spot is emitted onto the surface of the steel strip 1. In this case also, the spot length L1 or L2 can be adjusted easily through the aperture 112. The line spot length L1 or L2 is equal with the cross section size of the laser beam passing through the aperture 112. According to this embodiment, with the aperture 112 and the focusing lens 113, which is spherical or cylindrical, it is possible to form various spot shapes on the surface of the steel strip 1 as shown in FIG. 4.

In a cold rolling of an iron and steel mill, several welding types are selectively performed according to the composition and thickness of steel strips, and welding shapes are varied according to such welding types. Where two coils are connected together via welding in the cold rolling, a strip or band-shaped weld is formed with a certain width as shown in FIGS. 1 and 2. This type of weld influences the performance of the light detector of the reflectivity measuring mechanism 110 with following factors:

(1) Laser beam reflectivity or absorbance of strip-shaped weld
(2) Surface roughness of strip-shaped weld
(3) Features of strip-shaped weld (roughness or bending)
(4) Width of strip-shaped weld Of these factors, factors (1) to (3) decide the amplitude of output at the light detector, and factor (4) decides the time slot of an output signal. Change in laser reflectivity at the weld is decided by the weld shape, which is varied according to the welding type. The welding type carried out in the cold rolling of the iron and steel mill includes flash butt welding, laser welding, mesh seam welding and so on. Where steel strips are relatively thick, butt welding is carried out by flash butt welding or laser welding. In case of a thin steel strip such as a steel sheet, lap welding is carried out by mesh seam welding.

FIG. 5 is a sectional view illustrating a weld shape formed by a flash butt welding according an embodiment of the invention. In the cold rolling of the iron and steel mill, flash butt welding is carried out in Pickling line tandem Cold Mill (PCM). Such a welding welds a first steel strip 51 to a second steel strip 52 and leaves a welding bead 53, which damages feed and mill rolls. To prevent it, trimming 54 is performed. A trimmed portion 55 reveals inner steel strip material, which has a very high glossiness (reflectivity to laser beam). Therefore, the weld forms a high glossy strip 55 with a width of a few tens of mm in the width direction of the steel strip. On the other hand, laser welding leaves a welding bead with a narrow width (e.g., 1 mm to 2 mm) and a small height. Since trimming is not carried out, the welding bead is followed by a crease or groove, thereby forming an irregular surface structure. The irregular surface structure of the welding bead mainly changes the reflecting angle of a laser beam to vary the output of the light detector of the laser reflectivity measuring mechanism 110. Mesh seam welding is applied to lap welding of thin steel strips, thereby forming a stepped weld. Steps of the weld correspond to the thickness of each steel strip 51 and 52 and extend in the thickness direction of the steel strips 51 and 52. The steps in the mesh seam weld also change the reflecting angle of a laser beam, thereby varying the output of the light detector of the laser reflectivity measuring mechanism 110.

FIG. 6 is a graph illustrating a weld detection signal by a laser reflection measuring mechanism according to an embodiment of the invention.

As described above, the output of the light detector of the laser reflectivity measuring mechanism 10 may be varied by different factors according to welding type. Accordingly, change in laser beam reflectivity at a weld as shown in FIG. 6 will be different also. To overcome such a problem of change in laser reflectivity according to welding type, the level of a reference signal for determining a weld (hereinafter will be shortly referred to as "weld-determining signal level") and the time interval of a signal for determining a weld (hereinafter will be shortly referred to as "weld-determining time interval" or "time interval") $\Delta T$ can be adjusted. That is, when the weld-determining signal level and weld-determining time interval $\Delta T$ are set according to welding type, on-line welding detection can be ensured stably regardless of welding type.

Referring to FIG. 6 again, in case of attempting to detect a weld on the basis of change in the reflectivity of the reflecting laser beam measured by the light detector, the weld can be detected more stably when the difference between the output of the light detector measured on an ordinary steel strip surface and that measured on the weld is greater and a detection signal of the light detector on the weld has a larger time interval. In FIG. 6, the reference sign $\Delta_{IN}$ indicates a reflectivity deviation measured on the surface of the steel strip 1, which originates from the vibration of the moving steel strip 1 or noises related with surface defects. When the weld passes through a detection point, change in the output of the light detector has an amplitude of $\Delta I_{WH} + \Delta I_{WL}$ with a time interval $\Delta T$. To detect the weld stably in FIG. 6, it is necessary to satisfy following condition.

$$\frac{xI_{WH} + xI_{WL}}{xI_N} K1 \qquad \text{Math Figure 1}$$

That is, it requires the amplitude of change in the output of the light detector $\Delta I_{WH} + \Delta I_{WL}$ to be very larger than the reflectivity deviation $\Delta_{IN}$ originating from strip vibration or surface detects. It is also required for the time interval $\Delta T$ of the change in the output of the light detector at the weld to be steady. When the time interval ΔT of the change in the output of the light detector is steady, it is possible to get rid of erroneous detection factors such as change in the output of the light detector owing to the surface defects of the steel strip. This is because that the time interval ΔT is not steady in general when the output of the light detector changes owing to the surface defects of the steel strip.

FIGS. 7 and 8 are graphs illustrating examples of laser reflection signals detected on a weld by the on-line detection system according to an embodiment of the invention.

The graph of FIG. 7 illustrates a waveform of a detection signal on a flash butt weld by the light detector, and FIG. 8 is on-line data produced in an actual cold rolling, which is a signal waveform acquired by increasing a circular spot as shown in (b) of FIG. 4 in the range from 1 mm to 30 mm. According to this embodiment, when the circular spot of the laser beam has a too small diameter, a signal indicating a weld is rarely discriminated from noises resulting from fine protrusions and indents on the surface of the steel strip. On the other hand, when the circular spot is too large, the light detector 11 itself outputs a too small value. Therefore, it can be understood that the weld signal is most easily detected when the spot diameter is in the range from 4 mm to 6 mm, and more preferably 5 mm. According to another embodiment, although not shown in the drawings, when a laser beam emitted forms a line spot onto the surface of the steel strip, detection may be performed easily when the line spot has a width ranging from 2 mm to 5 mm and a length ranging from 30 mm to 50 mm. These data on the line spot are results obtained through a number of experiments, which show that a reflection laser beam is easily detectable at such width and length.

The optimum size of the circular spot and/or the optimum shape thereof as shown in FIG. 6 may be varied according to welding type. Thus, when optimum spot size and shape are selected, a weld can be easily detected on-line according to the invention from any welding types currently performed in the cold rolling of an iron and steel mill.

In the graph of FIG. 7, when the laser beam reflects from the surface of the steel strip 1, the reflectivity has a significant difference between a reflectivity signal level A detected from an ordinary steel strip surface and a reflectivity signal level B detected from the weld. The two reflectivity signal levels are compared with each other to locate the weld. In particular, when the reflectivity signal level at a specific point is a preset reference signal level or indicative waveform level $\Delta I_{WL}$ or more, the specific point is determined as a weld.

FIG. 9 is a flowchart illustrating an on-line detection method for a weld of a steel strip according to an embodiment of the invention.

Referring to FIG. 9, a laser beam for emission onto the surface of the moving steel strip 1 is generated in S900, and its cross section is adjusted in S902. Here, the step S902 of adjusting the laser beam cross section may be selectively executed. The laser beam is focused with the focusing lens 112 in S904, and emitted onto the surface of the moving steel strip 1 in S906. Here, the laser beam is emitted onto the surface of the steel strip 1 preferably at a right angle.

As the laser beam is emitted onto the surface of the steel strip 1, the laser beam is reflected from the surface. The reflecting laser beam is detected continuously in S908, and its reflectivity is extracted in S910. The reflectivity of the reflecting laser beam is an index indicating the intensity thereof. When the reflectivity of the reflecting laser beam extracted continuously shows an intensity larger than a preset threshold value at a specific point or interval, this point or interval is determined as a weld in S912 and S914.

In this process, the laser beam reflecting from the surface of the steel strip is continuously detected to locate the weld based on the difference between the reflectivity signal on the weld and that on the ordinary portions of the steel strip.

In the step S912 above, when the reflectivity signal level is larger than the preset threshold level and the reflectivity signal width is within a predetermined range, a corresponding point would be determined as a weld. This is to discriminate the actual weld from a situation where noises owing to protrusions and indents give an instantaneous and sharp rise to the signal level.

As described above, the one-line detection system and method for a weld of a steel strip may include at least two of the laser reflectivity measuring mechanism 110. In this case, it is possible to detect a weld by using a detection signal from any one of the laser reflectivity measuring mechanism 110 or combining two or more detection signals. This is because to discriminate the weld or the strip 55, which is extended in a width direction of the steel strip, from high glossy surface defects which are formed locally. Since such localized high glossy surface defects do not have a uniform configuration, when the reflectivity is measured from two or more points in the width direction of the steel strip, it is highly unlikely that equal detection signals can be acquired from two or more defects. Accordingly, when more reflectivity measuring mechanisms 110 are installed in the width direction of the steel strip, erroneous detection resulting from surface effects will occur less.

According to certain embodiments of the invention as set forth above, a weld moving at a high speed can be easily detected on-line without using a through hole as in the prior art. Furthermore, since a through hole is not necessary, productivity of cold rolled products can be enhanced and problems such as marking and fracture can be essentially excluded.

Moreover, according to certain embodiments of the invention, it is possible to detect a weld easily and precisely on-line by emitting a laser beam continuously onto a steel strip and locating the weld based on the reflectivity difference between the weld and an ordinary steel strip surface.

It is to be understood that while the present invention has been illustrated and described in relation to certain embodiments in conjunction with the accompanying drawings, such embodiments and drawings are illustrative only and that the present invention is in no event to be limited thereto. Rather, it is contemplated that modifications and equivalents embodying the principles of the present invention will no doubt occur to those of skill in the art. It is therefore contemplated and intended that the invention shall be defined by the full spirit and scope of the claims appended hereto.

The invention claimed is:

1. An on-line detection system for a weld of a steel strip comprising:
   reflectivity measuring means for emitting a laser beam onto a moving steel strip and continuously measuring a reflectivity of the laser beam returning from a surface of the steel strip; and
   signal processing means for detecting the weld of the steel strip based on change in a reflectivity measured on the weld,
   wherein the reflectivity measuring means includes:
   a laser beam generator for generating the laser beam;
   a focusing lens for focusing the laser beam;
   a collecting lens for collecting the laser beam reflecting from the surface of the steel strip;
   a light detector for outputting an electric signal corresponding to a reflectivity of the collected laser beam; and a beam adjuster for adjusting a cross section of the laser beam generated by the laser beam generator, wherein the signal processing means adjusts a weld-determining signal level and a weld-determining time interval according to a welding type.

2. The on-line detection system of claim 1, wherein the beam adjuster adjusts the laser beam emitted onto the surface of the steel strip into a circular spot having a diameter of 4 mm to 6 mm or a line spot having a width of 2 mm to 5 mm and a length of 30 mm to 50 mm.

3. The on-line detection system of claim 1, wherein the focusing lens comprises a spherical lens or a cylindrical lens.

4. The on-line detection system of claim 1, wherein the laser beam emitted onto the surface of the steel strip has a shape selected from a group consisting of a point, a circle and a line.

5. The on-line detection system of claim 1, wherein the signal processing means determines a specific point on the surface of the steel strip as the weld if a reflectivity of the laser beam returning from the specific point is out of a preset threshold value.

6. The on-line detection system of claim 1, wherein the reflectivity measuring means emits the laser beam continuously at an angle ranging from 80° to 100° with respect to the surface of the steel strip.

7. The on-line detection system of claim 6, wherein the reflectivity measuring means emits the laser beam perpendicularly to the surface of the steel strip.

8. An on-line detection method for a weld of a steel strip, comprising steps of:
(a) emitting a laser beam onto a surface of a steel strip which is being transported;
(b) continuously detecting the laser beam reflecting from the surface;
(c) measuring a reflectivity of the reflecting laser beam; and
(d) locating the weld based on change in the reflectivity,
wherein step (a) generates the laser beam and focuses the laser beam on the steel strip being transported,
wherein step (a) further comprises adjusting a cross section size of the laser beam generated, and
wherein step (c) further comprises adjusting a weld determining signal level and a weld-determining time interval according to a welding type.

9. The on-line detection method of claim 8, wherein the step (a) emits the laser beam perpendicularly onto the surface of the steel strip.

10. The on-line detection method of claim 8, wherein the step (b) continuously detects the laser beam reflecting from at least two points arranged in a width direction of the steel strip.

11. The on-line detection method of claim 8, wherein the step (d) comprises determining a specific point on the surface of the steel strip as the weld if the reflectivity of the laser beam returning from the specific point is out of a preset threshold value.

* * * * *